United States Patent
Roesler

(10) Patent No.: US 11,124,336 B2
(45) Date of Patent: Sep. 21, 2021

(54) PROTECTIVE CAP OR CONTAINER WITH LID AND SPRING-LOADED OPENING

(71) Applicant: Thiemo Roesler, Wangen (DE)

(72) Inventor: Thiemo Roesler, Wangen (DE)

(73) Assignee: ROESLER IP GMBH, Hergensweiler (DE)

( * ) Notice: Subject to any disclaimer, the term of this patent is extended or adjusted under 35 U.S.C. 154(b) by 410 days.

(21) Appl. No.: 16/141,002

(22) Filed: Sep. 25, 2018

(65) Prior Publication Data

US 2019/0092537 A1 Mar. 28, 2019

(30) Foreign Application Priority Data

Sep. 26, 2017 (DE) .......................... 102017122259.6

(51) Int. Cl.
| | |
|---|---|
| *B65D 43/16* | (2006.01) |
| *A61B 50/30* | (2016.01) |
| *A61B 50/20* | (2016.01) |
| *B65D 43/22* | (2006.01) |
| *A45D 40/22* | (2006.01) |

(Continued)

(52) U.S. Cl.
CPC ............ *B65D 43/162* (2013.01); *A61B 50/20* (2016.02); *A61B 50/30* (2016.02); *B65D 43/22* (2013.01); *A45D 2040/227* (2013.01); *A61B 2050/0056* (2016.02); *B65D 50/046* (2013.01); *B65D 2543/00194* (2013.01); *B65D 2543/00296* (2013.01); *B65D 2543/00351* (2013.01);

(Continued)

(58) Field of Classification Search
CPC .... B65D 43/162; B65D 43/22; B65D 43/168; B65D 43/166; B65D 11/188; B65D 50/046; A61B 50/20; A61B 50/30; A61B 2050/0056
USPC ................ 220/827, 833, 838, 839, 829, 847
See application file for complete search history.

(56) References Cited

U.S. PATENT DOCUMENTS

| | | | | |
|---|---|---|---|---|
| 3,968,880 A | * | 7/1976 | Ostrowsky | ........... B65D 43/162 |
| | | | | 206/540 |
| 5,293,993 A | * | 3/1994 | Yates, Jr. | ............ A61M 5/3205 |
| | | | | 206/365 |

(Continued)

FOREIGN PATENT DOCUMENTS

| | | |
|---|---|---|
| CH | 619413 | 9/1980 |
| DE | 602004010654 | 12/2008 |

(Continued)

*Primary Examiner* — James N Smalley
*Assistant Examiner* — Jennifer Castriotta
(74) *Attorney, Agent, or Firm* — Dentons Cohen & Grigsby P.C.

(57) ABSTRACT

A protective cap or container with a resilient opening is disclosed. The container generally includes top and bottom parts connected to each other via a film joint in a unilaterally pivotal fashion, and latched to each other in the closed state, with the top part being biased under the resilience of a repeatedly profiled resilient body in the opening direction in reference to the bottom part such that upon actuation of the latching device the top part pivots open from the bottom part under the force of resilience it is pivoted open and remains in the open position, with here the repeatedly profiled resilient body being made from a soft-elastic elastomer plastic material and fastened unilaterally at flaps connected thereto with the same material, at the two facial sides of the top part and the bottom part.

18 Claims, 10 Drawing Sheets

(51) Int. Cl.
*A61B 50/00* (2016.01)
*B65D 50/04* (2006.01)

(52) U.S. Cl.
CPC .......... *B65D 2543/00574* (2013.01); *B65D 2543/00888* (2013.01)

(56) References Cited

U.S. PATENT DOCUMENTS

| | | | | |
|---|---|---|---|---|
| 5,346,069 | A * | 9/1994 | Intini | B65D 21/0233 |
| | | | | 206/531 |
| 6,021,901 | A * | 2/2000 | Wolfe | B65D 43/162 |
| | | | | 206/1.5 |
| 8,162,144 | B2 * | 4/2012 | Intini | B65D 83/0463 |
| | | | | 206/532 |
| 2006/0283869 | A1 * | 12/2006 | Soncini | A45C 13/005 |
| | | | | 220/836 |
| 2007/0062964 | A1 * | 3/2007 | Kampf | B65D 43/22 |
| | | | | 220/835 |
| 2012/0055929 | A1 * | 3/2012 | Hayton | B65D 50/045 |
| | | | | 220/324 |

FOREIGN PATENT DOCUMENTS

| | | |
|---|---|---|
| DE | 602005004804 | 3/2009 |
| EP | 0839735 | 5/1998 |
| EP | 0873944 | 10/1998 |
| EP | 1799577 | 6/2007 |

\* cited by examiner

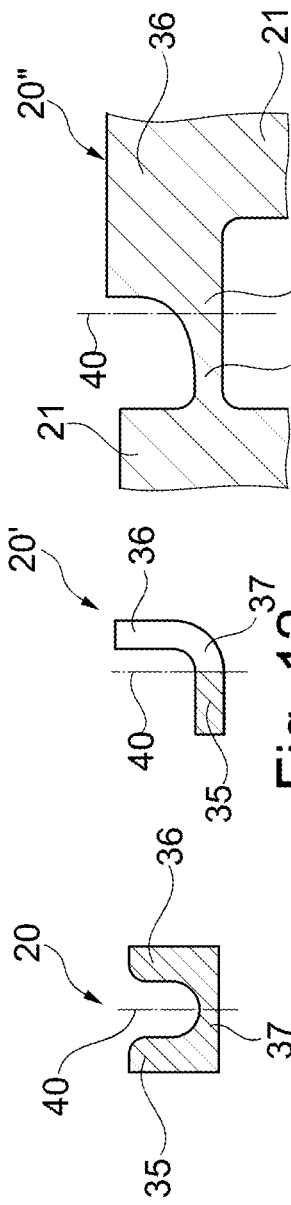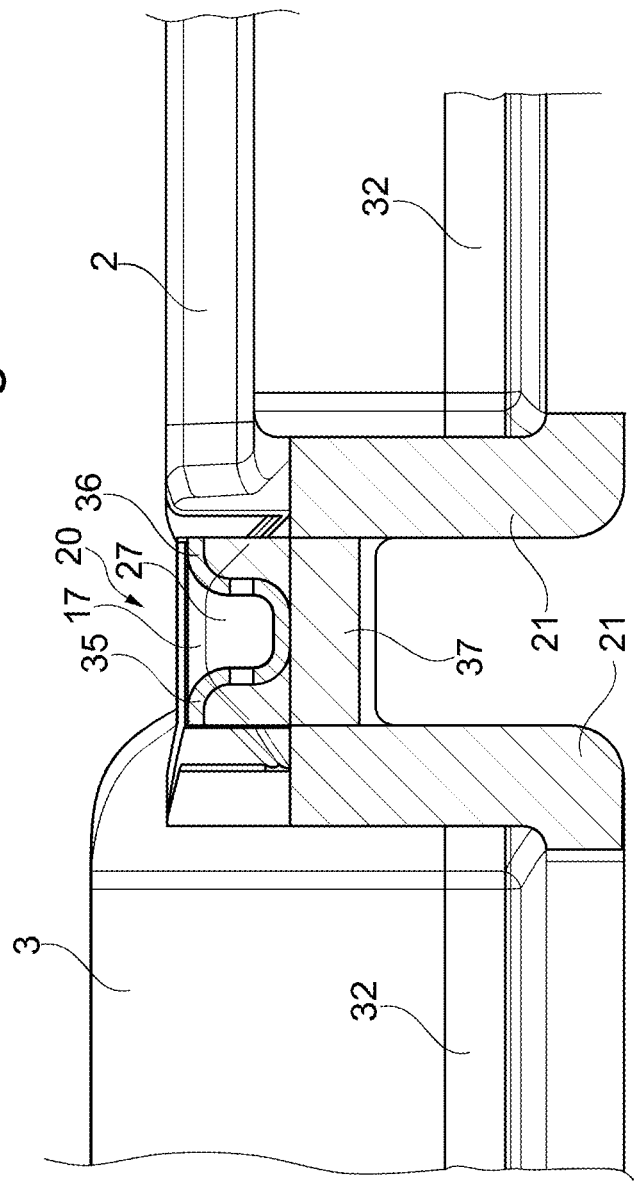

PROTECTIVE CAP OR CONTAINER WITH LID AND SPRING-LOADED OPENING

CROSS REFERENCE TO RELATED APPLICATIONS

This application claims priority to German Patent Application DE 10 2017 122 259.6, filed Sep. 26, 2017, incorporated herein by reference.

FIELD OF THE INVENTION

The invention relates to a protective cap or a container with a lid and a spring-loaded opening. The container is characterized in that the joint arrangement between a lid and a container is equipped with a resilient elastomer part. In this way, when opening a closing unit, the lid can automatically spring open in the area of its pivotal axis by the force of the resilient elastomer part, thus generating a container with a lid comprising a spring-loaded opening.

It is characterizing for this construction that a pivotal axis is arranged with a resilient elastomer part at the outside of the lid, such that when the lid is in the closed position the resilient elastomer part is biased under the spring force in the opening direction.

BACKGROUND OF THE INVENTION

Containers with lids having spring loaded openings are known, for example, with the object of DE602005004804T2 (EP1799577B1). In this prior art construction, the engagement point of the force of the resilient elastomer part is located at the lid. For this purpose, the pivotal axis of the joint is moved outwardly beyond the outer wall of the container.

By the distanced arrangement of the resilient elastomer part from the pivotal axis between the lid and the bottom part of the container the resilient elastomer part is biased when the lid is closed so that upon activation of the closing unit the lid automatically springs open. This is called the spring-loaded opening of the lid.

The joint arrangements or prior art at the outside of the container has largely proven in practice, however it is disadvantageous here that a major structural expense is necessary to produce such a joint arrangement.

The joint arrangement of prior art comprises a joint pin, which is encompassed by a joint bearing, which involves a high constructive production expense.

The arrangement of the resilient elastomer part, formed as a simple, planar, and band-shaped elastomer tape, is expensive as well, because it must be connected between two legs at the container, located outside the container arrangement, via suitable connection sites.

This results in the disadvantage that by the external arrangement of the legs at the outer walls of the container, the risk is that the legs could break, which are unprotected. If such a container falls to the ground, the risk is that the legs could break off.

Furthermore, the structural expense when generating the connection sites at the legs projecting from the container walls is expensive and not reliable in its operation regarding the fastening of the resilient elastomer tape.

The spring force of such a resilient spring arrangement is also limited since the resilient elastomer band shows only a short span length and thus, no strong resilient opening force is given or, in case of high tension forces, there is a risk that the resilient spring tape could tear or malfunction.

Based on the band-shaped embodiment of the resilient elastomer part, here the disadvantage is that all bending processes occur only via the planar elastomer band, showing a rectangular cross-section, which may lead to a shortened life span.

The object of CH 619 413 A5 has been disclosed as a bottle cap for fixed and deformable containers in which a tension body is provided at the bottle cap, biased in the opening direction, which is connected in one piece with the same material of the bottle wall and the cap and shows an approximately U-shaped profile. Such a bottle cap is not designed for a long life span with a plurality of various load changes.

Since the resilient body is made from the same, harder material as the material of the cap, it is subject to the disadvantage that strong tension force cannot be yielded over a long life span. Rather, in case of extended use, the risk of breaking develops for the tension body. The tension force shall be designed only with such strength that the bottle cap pivots sufficiently far away from the bottle opening without here a defined open position being required.

SUMMARY OF THE INVENTION

The invention is therefore based on the objective to further develop a protective cap or a container with an improved resilient opening. The container of the presently disclosed invention includes top and bottom parts connected to each other via a film joint in a unilaterally pivotal fashion, and latched to each other in the closed state, with the top part being biased under the resilience of a repeatedly profiled resilient body in the opening direction in reference to the bottom part such that upon actuation of the latching device, the top part pivots open from the bottom part under the force of resilience and remains in the open position. The repeatedly profiled resilient body may be made from a soft-elastic elastomer plastic material and may be fastened unilaterally at flaps connected thereto with the same material, at the two facial (hinge) sides of the top part and the bottom part, such that a resilient opening is formed between two opposite container parts showing a long life span and high tension force and with operating safety.

The resilient body is here provided at both sides in one piece with elastomer flaps made from the same material and each flap is penetrated with a slot at the respective face of the container wall and continues here in the form of an elastomer connection web. This leads to the advantage that a long span length of the resilient body is ensured, and that the resilient body can withstand a high number of load changes at high spring force and the life span is extended here.

Experience has shown that the repeatedly profiled resilient body is formed in its profile either as a U-shaped profile or one deviating from a U-profile, for example showing an L-shaped or triangular profile. In one variant it is preferably also embodied in a corrugated fashion, which means that the U-shaped profile is doubled or tripled when seen from the side.

In a preferred embodiment it is provided that the profiled resilient body is not connected directly at the facial sides of the container parts allocated to each other but extends in the form of an elastomer connection web into the interior of the two container parts.

In a first embodiment of the present invention, a container is provided, formed approximately like the one in EP1799577B1, which means it comprises a bottom part and a top part and forms a closed interior compartment in which different objects can be contained.

Such a container may represent, for example, a powder compact, a container for holding small parts, or the like.

In a preferred embodiment of the present invention, it is provided, though, that the container is formed as a protective cap for the protection of tips of surgical instruments, which differs from containers of prior art, such that the face of the protective cap is embodied as the opening side in which for example the tip of a surgical instrument to be protected or another sensitive object can be inserted. However, in one container the opening side of the protective cap is closed by a facial container wall.

Otherwise, the same parts of a container or a protective cap are subject to the same explanations with the difference between a protective cap and a container comprising that the container shows an interior cavity, which is closed per se, covered by a top part, while a protective cap according to the present invention forming an opening side at a facial side, located opposite the joint arrangement, embodied as an insert side, in which a medical object or a tool to be protected, such as a knife, a drill bit, or the like can be inserted.

The following description refers to a protective cap, however it can also be applied likewise to a container according to the object of EP1799577B1.

It is advantageous when the protective cap in its interior shows rib packages opposite each other, with one rib package being arranged at the interior of the top part and the opposite rib package at the interior of the bottom part and the two rib packages forming between each other a clamping seat, which helps the inserted object to be protected from being pulled out.

Such rib packages comprise individual, bendable elastomer ribs arranged behind each other at a mutual distance, which may show arbitrary shapes and contours.

They may be arranged opposite and aligned to each other, but they may also be arranged offset in reference to each other in order to form barb-like projections for the object to be inserted here.

Instead of an embodiment of rib packages comprising individual elastomer ribs arranged parallel and mutually distanced from each other, here different seats or protective or clamping devices may be used as well, such as elastomer pressure cushions, which also form a clamping seat between each other.

In this case, one elastomer cushion is arranged at the interior of the top part and the other elastomer cushion at the interior of the bottom part and they form therefore a clamping seat between each other.

In case of an embodiment of a container as a protective cap according to the object of the present invention, activation of the latching device may not be arranged at the opening side, in which the object to be protected is inserted, but the activation may occur preferably at the two lateral walls, opposite each other, between the top part and the bottom part, namely laterally adjacent to the opening side at the facial wall. This is the object of the an embodiment of a protective cap or container with a resilient opening, comprising a top part and a bottom part connected to each other via film joints in a unilaterally pivotal fashion and latched to each other in the closed state, with the top part under the resilience of a repeatedly profiled resilient body being biased in the opening direction in reference to the bottom part, so that upon actuating the latching device, the top part is pivoted open from the bottom part under the force of the resilience and remains in the opened position. In this embodiment, the latching device may be arranged between the top part and the bottom part at the lateral walls.

The features of this latching device shall be protected by themselves as well as in combination with the features of the embodiment of the resilient body.

Such a latching operation may comprise handles projecting from the lateral walls of the container, preferably embodied with round profiles or in a rounded shape. If respective pressure is applied with two fingers upon the operating handles positioned opposite each other (e.g., pressure applied on the handles toward the center of the protective container), the handles elastically move inwardly, here utilizing the elastomer resilient features of the lateral walls of the bottom part and simultaneously entrain the latching link connected to the respective operating handle, which this way disengages a latching recess arranged at the top part.

Instead of such an opening device, manually operated with the fingers, of course all other known operating devices may be used, such as magnetic closures, any latching means, VELCRO, adhesive tapes, or the like.

The invention is not limited to the specific arrangement of operating handles opposite each other with latching links formed thereat, although this embodiment is particularly preferred when the protective cap according to the invention is used with a resilient function according to the invention for the protection and acceptance of sensitive surgery instruments, such as scalpels, bone saws, or tweezers.

In the operating room, the protective cap can be grasped by the fingers of the gloved hand. Here, the two operating handles are pressed towards each other in order to disengage the latching links connected thereto from the latch recesses in the top part such that due to the spring force of the resilient body the top part automatically opens up and remains in this opened position.

By the use of a profiled resilient body, here a considerably stronger spring force develops compared to the use of a short, band-shaped body so that even heavy top parts can be opened with a strong spring force from the bottom part, and based on the fact that the resilient body is formed as an elastomer part showing a different material than the container walls, in addition to a strong spring force, a long life span results as well and a superior fastening method, because the resilient body extends with the corresponding flaps directly into the top part and the bottom part and is here connected to a connection web at the inside of the container.

By making the resilient body from a soft-elastic material, which is molded in a 2k-injection molding process to the container wall made from a harder material, here the advantage of a strong tensile force results with a long life span, without this leading to restrictions regarding the feasibility regarding the container walls made from a hard material.

By continuing the repeatedly profiled resilient body in the form of a flap connected thereat in one-piece, forming a single part with the resilient body made from the same material, here a particularly long span length results for the resilient body, which has not been known from prior art.

In a variant of the invention, it is provided furthermore that the resilient body, together with the flap connected thereat and made from the same material, is formed as a 2K-injection molded part, this means directly injected into the cups of the top and the bottom part, which show harder materials.

Here it is particularly advantageous that the resilient body continues with the flaps in the rib package, connected thereto and made from the same material, which means that the ribs of the rib package are also formed from the same material in one piece with the flap connected thereto.

This results in the advantage that in a single injection molding process, the entire resilient elastomer body made from a soft-elastic material can be connected to the harder elastic materials of the cups of the top and the bottom part, and also in case of a plurality of load changes, there is no longer a risk of breakage.

It is particularly advantageous to form the resilient body also such that a closed protective cup, which must remain under spring bias of the resilient body for many months in this stressed position, shows no loss of resilience.

By the particular embodiment of the profiled, for example corrugated, resilient body with its direct connection to the faces of the walls of the top and the bottom part, here on the one hand strong spring forces develop and on the other hand a long life span while maintaining the resilience over a long period of time because a very long span length is ensured for the resilient body.

The object of the present invention is not only discernible from the objective of the individual claims but also from the combination of individual claims with each other.

All information and features disclosed in the documents, including the abstract, particularly the spatial embodiment shown in the drawing is claimed as essential for the invention, to the extent they are new individually or in combinations in reference to prior art.

BRIEF DESCRIPTION OF THE DRAWINGS

In the following, the invention is explained in greater detail based on only one embodiment shown in the drawings. Here, the features and advantages of the invention relevant for it are discernible from the drawings and their description.

FIG. 10 shows a view of a central cross-section of the joint arrangement taken along line VI of FIG. 8.

FIG. 11 shows a view of a central cross-section of the resilient body of the joint arrangement taken along line VI of FIG. 8.

FIG. 12 shows an alternative embodiment of the resilient body illustrated in FIG. 11.

FIG. 13 shows another embodiment of the resilient body illustrated in FIG. 11, wherein the resilient body and the connection to the flaps connected thereto are formed of the same material.

DETAILED DESCRIPTION OF THE INVENTION

Figure 1:
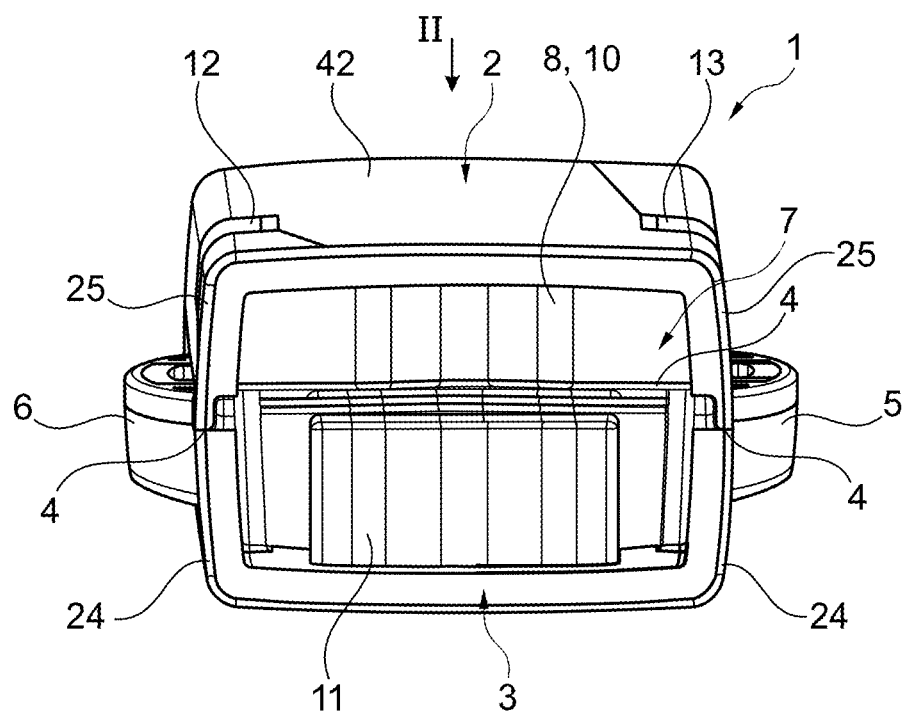
FIG. 1 shows a perspective view of a protective cap according to the invention viewed from the opening side.
Figure 2:
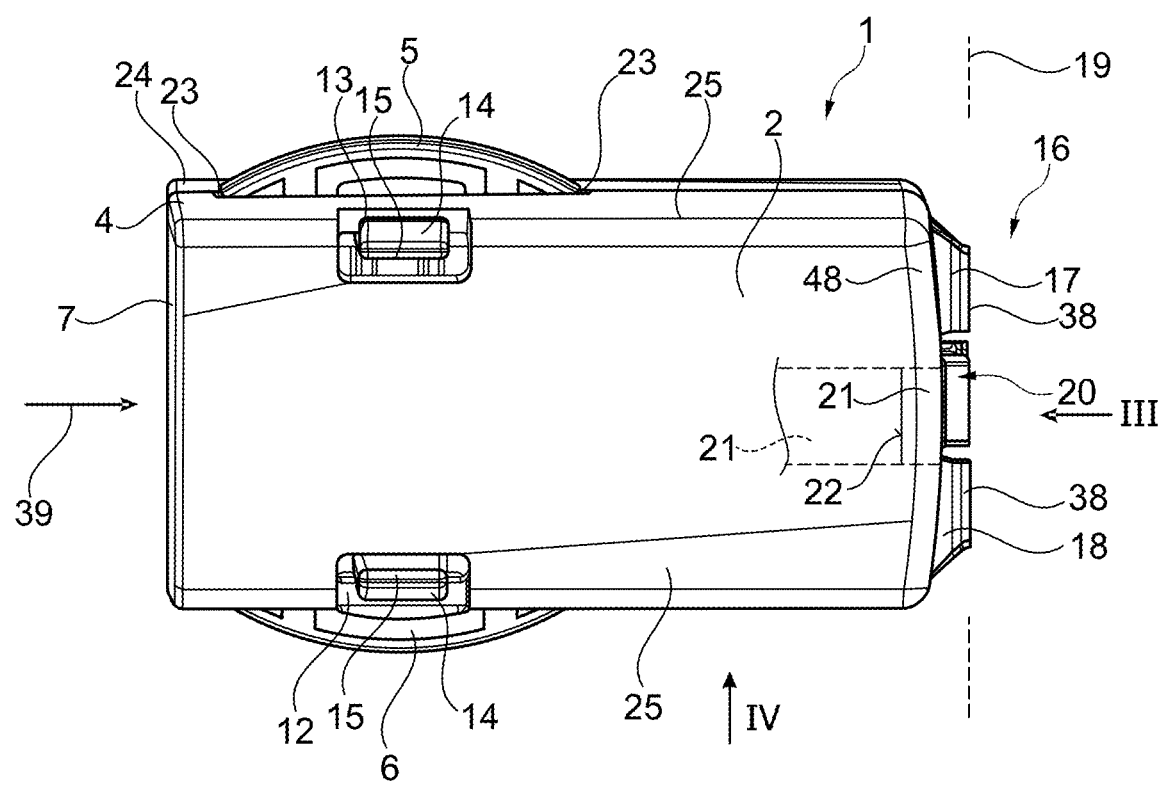
FIG. 2 shows a view of the protective cap illustrated in FIG. 1 viewed in the direction of arrow II (top side) of FIG. 1.
Figure 3:
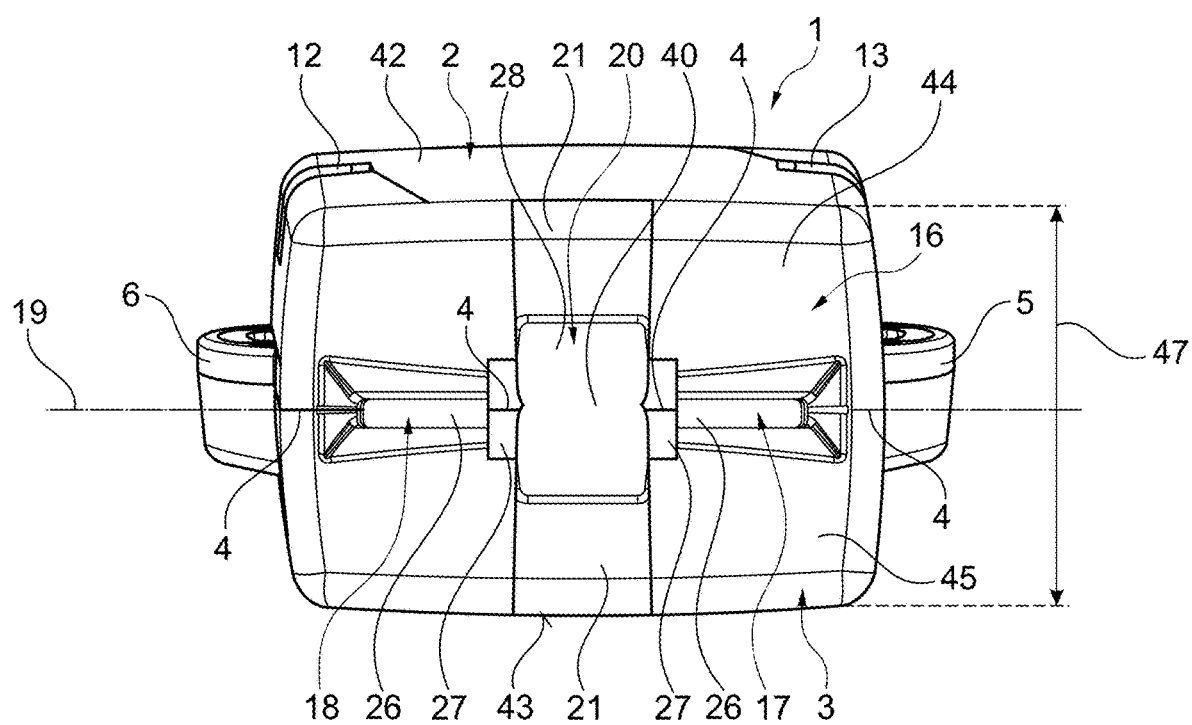
FIG. 3 shows a view of the protective cap illustrated in FIGS. 1 and 2 viewed in the direction of arrow III (hinge side) of FIG. 2.

FIGS. 1-3 show a protective cap 1 comprising a cup-shaped top part 2, which can latch in a form-fitting fashion via a separating seam 4 on a bottom part 3. The latching closure is actuated via two operating handles 5, 6 located opposite each other, with the operating handles 5, 6 being arranged in the respective lateral walls 24 of the bottom part 3.

The cup-shaped top part 2 forms the cover area 42, which in a rounded form transfers into two lateral walls 25 located opposite each other.

According to FIGS. 1 and 2, the protective cap 1 forms on the one side an opening side 7, in which the tool to be protected or the tip of a medical instrument can be inserted in the direction of the arrow 39 into the interior of a cup-shaped top and bottom part (2, 3) allocated to each other.

The insert opening of the opening side 7 may be limited by rib packages 10, 11 opposite each other, forming a clamping opening, so that the object to be inserted here is held in a force-fitting fashion by the clamping force of the holding ribs 8, 9 of the respective rib packages 10, 11.

Figure 5:
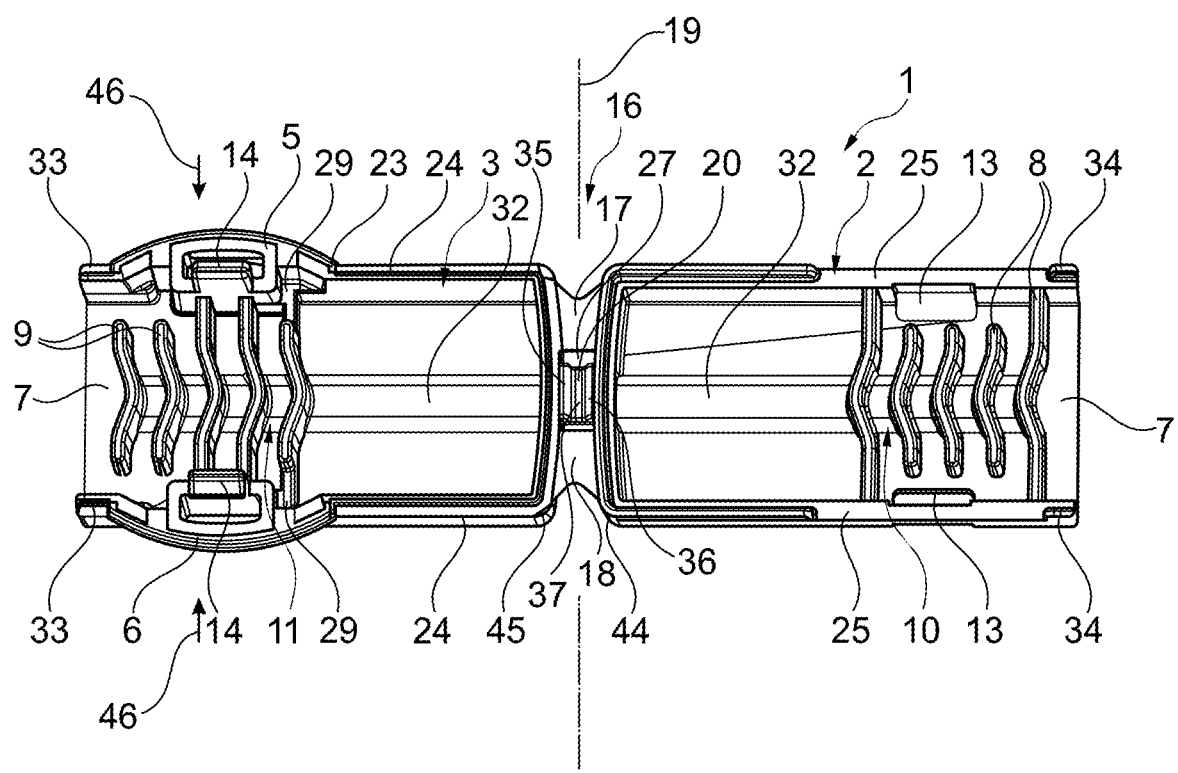
FIG. 5 shows a perspective view of the protective cap when in the open position (i.e., inside of protective cap).
Figure 6:
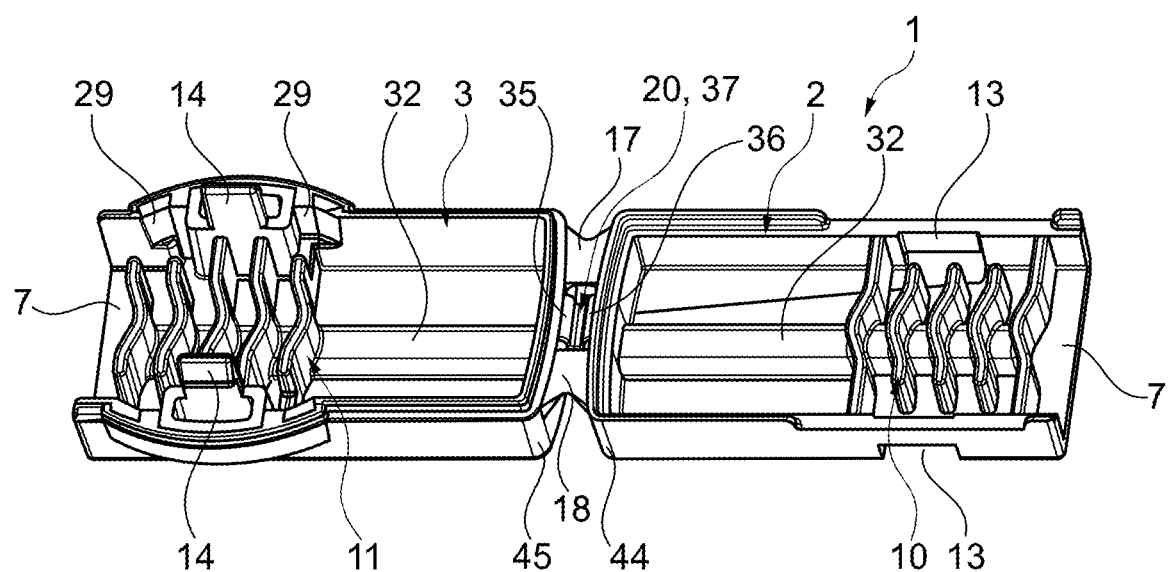
FIG. 6 shows a top view of the inside of the protective cap illustrated in FIG. 5.

FIGS. 5 and 6 show for example a plurality of contoured elastomer holding ribs 8, 9, arranged parallel and at a mutual distance, which are aligned to each other in the exemplary embodiment shown.

Similarly, the holding ribs 8 of the top part 2 can be arranged offset in reference to the holding ribs 9 of the bottom part 3, so that a stronger clamping effect is yielded upon an object inserted in the opening side 7 when they are engaging each other. A particular advantage, as disclosed in the general description, is the fact that the resilient body 20, to be described in the following, applies the spring force upon the joint arrangement 16 and continues in the form of two elastomer connection webs in the material of ribs 8, 9 so that in a preferred embodiment of the invention it is provided that the resilient body 20 is connected by the same material (one-piece-material) with the connection webs 32 and the holding ribs 8, 9 injection molded at the inside of the cup-shaped top and bottom parts 2, 3.

The invention is not limited to this embodiment. It may also be provided that the connection webs 32 are completely omitted and that the holding ribs 8, 9 are made from a completely different material than for example the resilient body 20.

The advantage of the embodiments shown in FIGS. 5 and 6 is however that both the resilient body 20 as well as the flaps 21 connected to the resilient body are made from the same material and that the connection webs 32 in turn form with the holding ribs 8, 9, made from the same material and connected to the flaps also made from the same material, a single elastomer part comprising a soft-elastic plastic.

The entire part may be produced in an injection molding process at the inside of the cup parts.

In addition to the arc-shaped contours of the holding ribs 8, 9 of course all arbitrary shapes of ribs may be used. They may also be embodied as pressure cushions, this means they are injected directly like cushions made from an elastomer material at the inside of respectively the top and bottom part 2, 3.

Such ribs can also be formed as punctual holding points or clamping points, and they may also be made from a hard material, which then results in an opening side 7 defined precisely in its shape for an instrument or tool to be inserted here.

The closing arrangement comprises two opposite operating handles 5, 6, arranged precisely symmetrical to each other. The operating handles 5 are for example embodied arc-shaped and connected via lateral connections 29 directly to the respective lateral wall 24 of the bottom part 3 using injection-molding technology.

By the elastomer plasticity of a connection 29 at the lateral walls 24 the advantage develops that upon pressure being applied to the operating handle 5, 6 in the direction of the arrow 46 the connections 29 elastically give way and thus the latching link 14 arranged in this area moves inwardly.

A latching link 14 is allocated to each operating handle 5, 6 and each latching link 14 engages a corresponding latching recess 13 in the area of the upper part 2.

Figure 4:
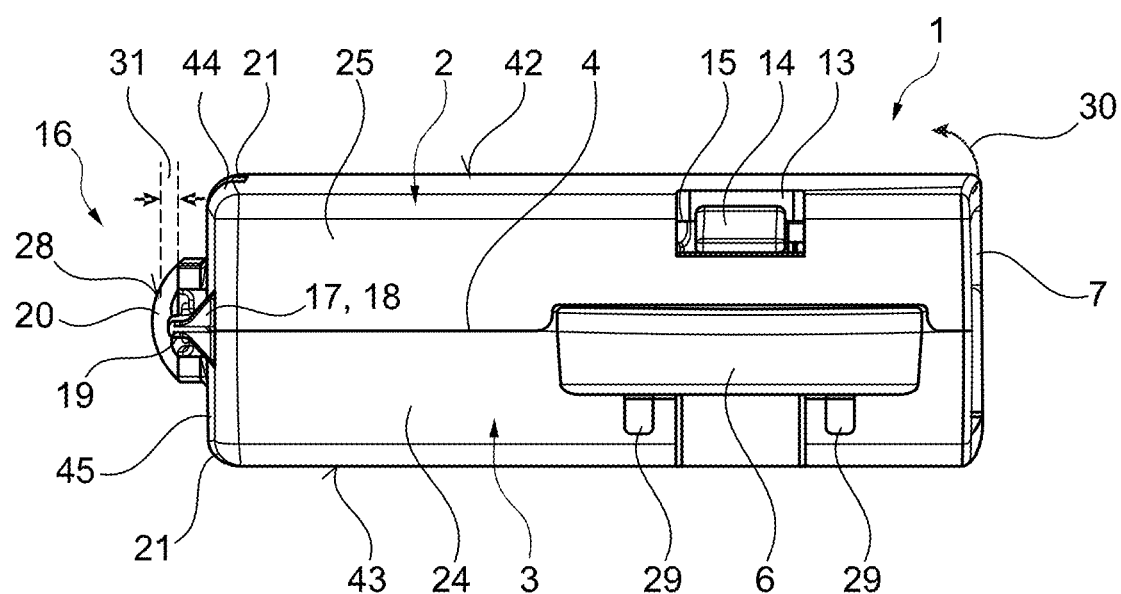
FIG. 4 shows a view of the protective cap illustrated in FIGS. 1 and 2 viewed in the direction of arrow IV (lateral side) of FIG. 2.

According to FIG. 4, the latching link 14 encompasses a housing-fixed latching edge 15 in the top part 2 in order to yield a latching between the top part 2 and the bottom part 3.

As soon as pressure is applied in the direction of the arrow 46 upon the operating handles 5, 6 with the fingers of a hand, the latching links are moved towards each other, reducing the mutual distance, and releasing the engagement with the latching recesses 12, 13 in the top part 2.

The lateral areas of the respective operating handles 5, 6 engage via the connection parts 23 the lateral walls 24 of the top part 2.

The connection parts 23 forms together with the elastomer connection 29 the elastomer return moment for the operating handle 5, 6, which are respectively spring-loaded in the opposite direction of the direction of the arrow 46.

A particular advantage is also the embodiment of a film joint and a resilient body with high spring force arranged centrally therebetween.

Figure 8:
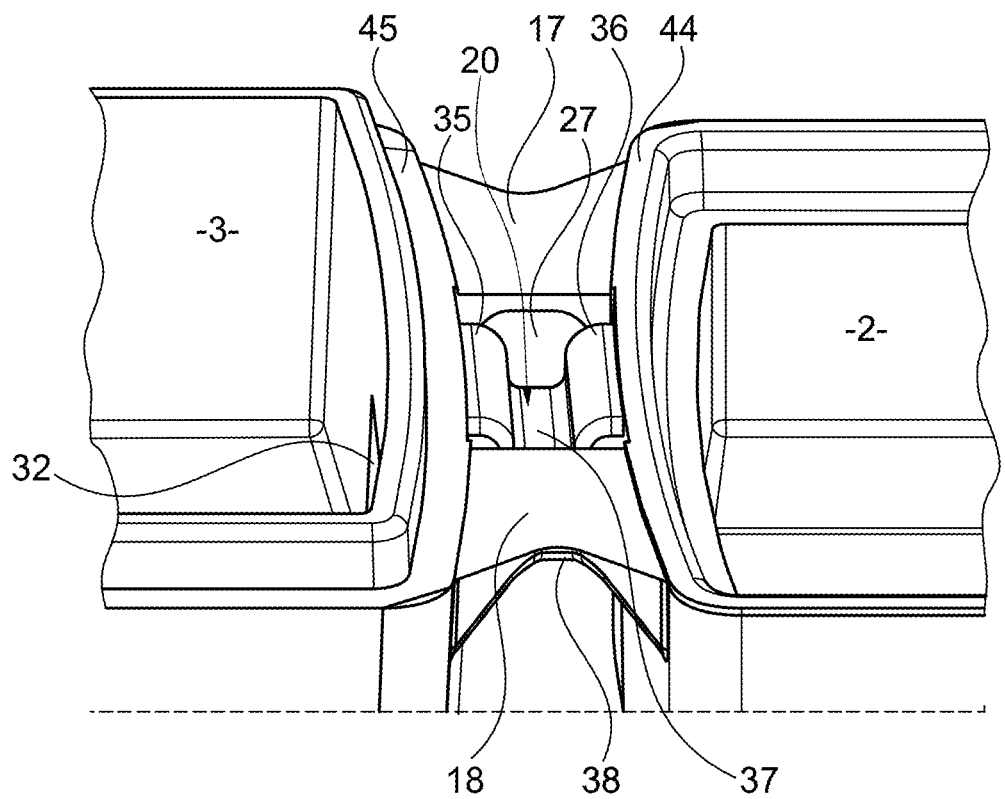
FIG. 8 shows a schematic view of the joint arrangement according to the invention, wherein two film joints are located opposite to each other and aligned to each other, and a resilient body is arranged centrally therebetween.

According to FIG. 3, in order to bridge the respective facial side 44 (hinge side) of the top part 2 towards the facial side 45 of the bottom part 3, respectively one film joint 17, 18 is used, which is profiled in an arced fashion according to FIG. 8 and forms a central bending line 38.

In this way it is ensured that the pivoting of the joint arrangement 16 occurs along the pivotal axis 19 between a facial side 44, 45 of the top part 2 and the bottom part 3 arranged allocated to each other (i.e., hinge side of the protective cap or container).

It is important according to FIG. 4 that the unlocking of the latching device of the top part 2 in the direction of the arrow 30 opens automatically under the resilience of the resilient body 20 and remains in this position.

It is discernible from FIG. 4 that the resilient body 20 is arranged as a massive body, deviating from the usual band structure, outside the pivotal axis 19 of the film joint 17 and bridges this pivotal axis.

By selecting the distance 31, the opening torque is defined in the direction of the arrow 30.

Figure 7:
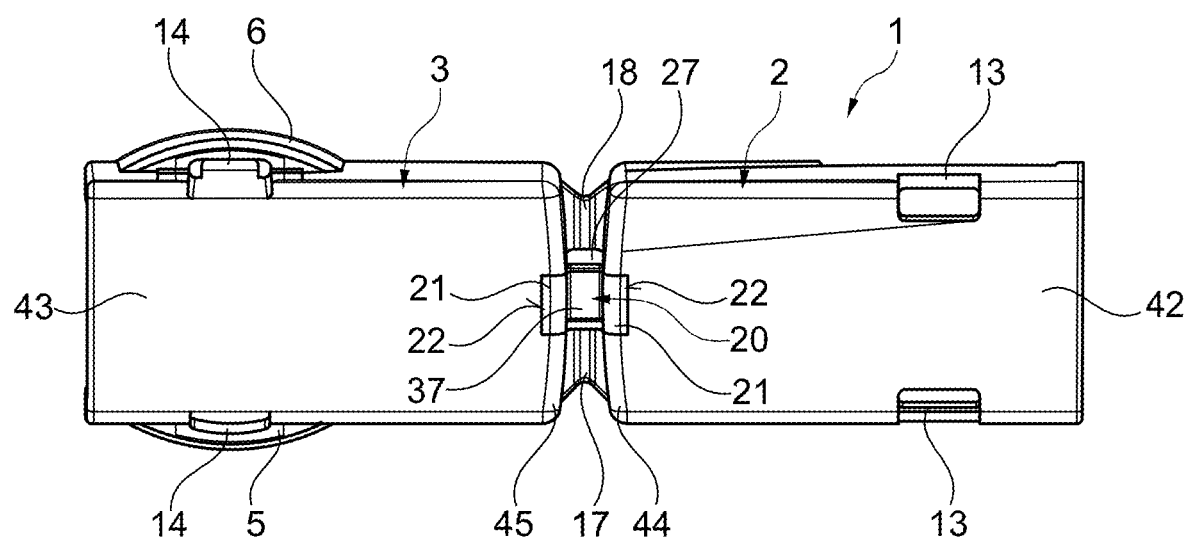
FIG. 7 shows a bottom view of the outside of the protective cap illustrated in FIG. 5.

A particularly long spring length develops according to the invention such that the resilient body 20 according to FIG. 7 continues with the same material into the flaps 21, which flaps 21 respectively engage the cover areas 42, 43 of the top and bottom parts and are connected with corresponding transfer edges 22 to the areas 42, 43 of the top part and the bottom part 2, 3.

This yields a particularly long spring length of the resilient body 20, which has not been known from prior art.

It is also particularly advantageous that the respective flaps 21, which are connected with the same material as the resilient body 20, continue inwardly at the interior of the cup-shaped top and bottom part 2, 3 like connection webs 32 and form a connection of the same material with the rib packages 10, 11 injected at the connection webs 32 in one piece.

It is particularly advantageous that in the central area between the film joints 17, 18 arranged aligned to each other now a repeatedly profiled resilient body 20 is arranged, which in the preferred exemplary embodiment (see FIG. 6, FIG. 7, FIG. 5, FIG. 8, and FIG. 11) is approximately arched or corrugated.

Figure 9:
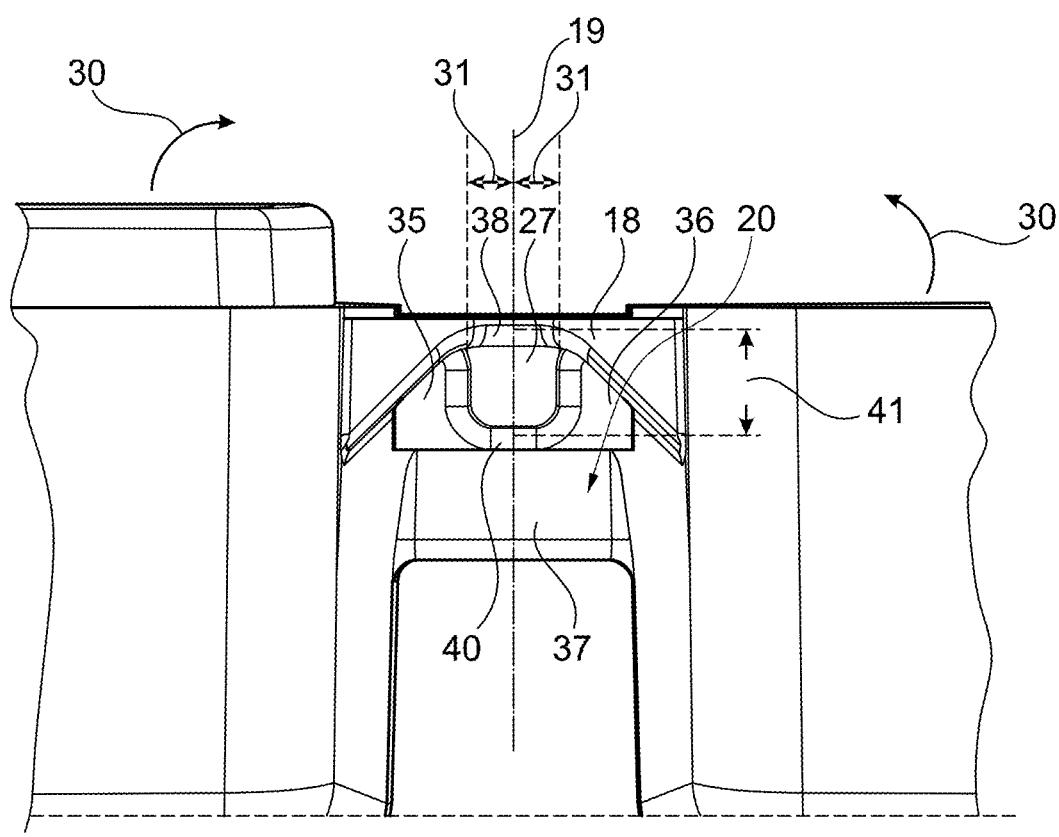
FIG. 9 shows a view of the joint arrangement illustrated in FIG. 8 viewed in the direction of arrow V (view of lateral side) of FIG. 8.

The facial sides 26 of the film joints form therefore bending lines 38 and the resilient body 20 arranged therebetween forms a spring edge 40, which is best shown in FIG. 9.

The resilient body 20 is profiled in a mirror-symmetrical fashion and comprises two opposite arc structures 35, 36 between which a central leg 37 is arranged made from the same material.

The arc structures 35, 36 continue in the same material in the flaps 21 and these in turn are connected to facial sides 44, 45 of the top and bottom part 2, 3 opposite each other.

This results in a particularly long spring length, which is marked as spring length 47 in FIG. 3.

The repeatedly profiled resilient body 20 is arranged in the area of a central release position 27 between film joints 17, 18 arranged side by side and aligned to each other.

The profiled resilient body 20 forms therefore an arched surface 28 (see FIGS. 3 and 4), which defines a central spring edge 40 by which the resilient body 20 deforms as an elastomer.

Thus, from the central spring edge 40 of the central leg 37 of the corrugated profiled resilient body 20 spaces 31 develop, which are respectively formed at the right and the left of the pivotal axis 19, with the spaces 31 defining the distance between the spring edge 40 and the arc structures 35, 36 of the resilient body 20.

The distance 41 describes the profile depth of the corrugated profiled resilient body 20 and the distance 41 influences the opening torque between the top part 2 and the bottom part 3.

The particular arc structure of the resilient body 20 is particularly discernible from FIGS. 8 and 9. The arc structures 35, 36 considerably increase the opening torque of the resilient body 20.

The distance 41 defines the depth of the corrugated structure developing between the lateral arc structures 35, 36 and the central leg 37.

FIG. 11 shows schematically an arc structure without displaying the lateral connections via the flaps 21 and the like. For the general implementation of the invention it is sufficient that the resilient body is embodied corrugated without it here being necessary that the form continues into the flaps.

The spring force is however increased by the continuation of the resilient body into the flaps.

FIG. 12 shows a modified exemplary embodiment of a profiled resilient body 20, in which it is discernible that the profile of the resilient body 20 can also be embodied as a simple L-profile, with then the two arc structures 35, 36 being no longer mirror-symmetrical to each other. The central leg 37 is also offset in reference to the spring edge 40.

A similar exemplary embodiment is also shown in FIG. 13, compared to FIG. 12, in which it is discernible that it is possible to form the central leg relatively thick and directly transfer a large-profile right arc structure 36, while the left arc structure 35 is formed smaller.

Here, too, the direct connection to the flaps 21 following thereto in the same material occurs such that a slightly differently profiled resilient body 20' is shown according to FIG. 12 or 20", according to FIG. 13.

In order to provide centering between the top part 2 and the bottom part 3 it is provided according to FIG. 5 that at the inside of the top part 2 centering recesses 34 are provided, which engage corresponding centering cams 33 at the bottom part 3, when the two parts 2, 3 are latched to each other.

| Legend of the drawings: |
|---|
| 1: Protective cap |
| 2: Top part |
| 3: Bottom part |
| 4: Separating seam |
| 5: Operating handle |
| 6: Operating handle |
| 7: Opening side |
| 8: Holding rib (top) |
| 9: Holding rib (bottom) |
| 10: Rib package (top) |
| 11: Rib package (bottom) |
| 12: Latching recess |
| 13: Latching recess |
| 14: Latching link |
| 15: Latching edge |
| 16: Joint arrangement |
| 17: Film joint |
| 18: Film joint |
| 19: Pivotal axis |
| 20: Resilient body 20', 20" |
| 21: Flap (of 20) |
| 22: Transitional edge |
| 23: Connection site |
| 24: Lateral wall (bottom part 3) |
| 25: Lateral wall (top part 2) |
| 26: Facial side (of 17, 18) |
| 27: Release |
| 28: Arc surface (of 20) |
| 29: Connection |
| 30: Direction of arrow |
| 31: Distance (between 19 + 20) |
| 32: Connection web |
| 33: Centering cam |
| 34: Centering recess |
| 35: Arc structure (of 20) |
| 36: Arc structure (of 20) |
| 37: Central leg (of 20) |
| 38: Bending line (of 17, 18) |
| 39: Direction of arrow |
| 40: Spring edge |
| 41: Distance (between 38 + 37) |
| 42: Cover area (of 2) |
| 43: Cover area (of 3) |
| 44: Facial side (of 2) |
| 45: Facial side (of 3) |
| 46: Direction of arrow |
| 47: Spring length |

What is claimed is:

1. A protective container with a resilient opening, the container comprising:
    a top part and a bottom part connected to each other along edges of adjacent hinge sides thereof via a film joint such that the top and bottom parts pivot between an open state and a closed state about a pivot axis;
    a latching device configured to maintain the top part and the bottom part in the closed state when the latching device is engage; and
    a resilient body made from an elastomeric material, wherein the resilient body is fastened via flaps on the adjacent hinge sides of the top and bottom parts,
    wherein the top part is biased into the open state via the resilient body such that upon actuation of the latching device the top part pivots open from the bottom part under the force of resilience of the resilient body and remains in the open state,
    wherein the resilient body continues with the flaps formed from the same material in the form of an elastomer connection web into an interior of each of the top part and the bottom part.

2. The protective container of claim 1, wherein the elastomer connection web is connected to rib packages arranged on an inside surface of the top and bottom parts at an opening end thereof, wherein rib packages comprise one or more individual, bendable elastomeric ribs arranged behind each other at a mutual distance.

3. The protective container of claim 2, wherein the elastomer connection web and the rib packages are formed of the same material.

4. The protective container of claim 1, wherein the elastomer connection web is connected to pressure cushions arranged on an inside surface of the top and bottom parts.

5. The protective container of claim 4, wherein the elastomer connection web and the pressure cushions formed of the same material.

6. The protective container of claim 1, wherein the latching device is positioned on an opening side of the top and bottom parts, wherein the opening side is opposite the hinge side.

7. The protective container of claim 1, wherein the latching device comprises lateral, opposite handles attached to opposite lateral sides of the protective container.

8. The protective container of claim 7, wherein the handles are connected to the respective lateral sides of the bottom part.

9. The protective container of claim 8, wherein at each handle a latching link is arranged and each latching link engages a corresponding latching recess in the top part.

10. The protective container of claim 1, wherein the resilient body is embodied with a U-shaped profile.

11. The protective container of claim 1, wherein the resilient body is embodied with a triangular profile.

12. A protective container with a resilient opening, the container comprising:
    a top part and a bottom part connected to each other along edges of adjacent hinge sides thereof via one or more film joints such that the top and bottom parts pivot between an open state and a closed state about a pivot axis;
    a latching device arranged between the top part and the bottom part at lateral walls thereof, wherein the latching device is configured to maintain the top part and the bottom part in the closed state when the latching device is engaged; and
    a joint arrangement comprising a resilient body and a pair of flaps made from an elastomeric material, wherein the resilient body is fastened via the flaps on the adjacent hinge sides of the top and bottom parts,
    wherein the top part is biased into the open state via the resilient body such that upon actuation of the latching device the top part pivots open from the bottom part under the force of resilience of the resilient body and remains in the open state,
    wherein the resilient body continues with the flaps formed from the same material in the form of an elastomer connection web into an interior of each of the top part and the bottom part.

13. The protective container of claim 12, wherein the latching device comprises lateral, opposite operating handles that engage a corresponding latching recess.

14. The protective container of claim 13, wherein operation of the operating handles to disengage the latching device comprises application of pressure on the operating handles in a direction toward a center of the protective container.

15. The protective container of claim 13, wherein the operating handles are directly connected via lateral connections to a respective lateral wall of the bottom part.

16. The protective container of claim 13, wherein the operating handles are positioned on the bottom part, and each operating handle comprises a latching link that engages the corresponding latching recess in the top part.

17. The protective container of claim 12, wherein the resilient body is embodied with a U-shaped profile or shows a corrugated form.

18. The protective container of claim 12, wherein the resilient body is embodied with a triangular profile.

* * * * *